US000001401H

United States Statutory Invention Registration [19]

[11] Reg. Number: H1401

Campbell

[43] Published: Jan. 3, 1995

[54] FUNGICIDAL OXAZOLIDINONES

[75] Inventor: Carlton L. Campbell, Newark, Del.

[73] Assignee: E. I. Du Pont de Nemours and Company, Inc., Wilmington, Del.

[21] Appl. No.: 152,617

[22] Filed: Nov. 15, 1993

[51] Int. Cl.[6] ..... A01N 55/10; A61K 31/695; C07D 263/04

[52] U.S. Cl. ..... 514/63; 514/309; 514/312; 514/314; 514/306; 514/376; 548/110; 548/226; 548/217; 546/152

[56] References Cited

U.S. PATENT DOCUMENTS 5,223,523 6/1993 Adams, Jr. et al. ..... 514/376

FOREIGN PATENT DOCUMENTS 9318016 9/1993 WIPO .

OTHER PUBLICATIONS

Geffken, Z. Naturforsch, B: Anorg. Chem., Org. Chem. (1983) 38B(8), 1008–1014.

*Primary Examiner*—Robert L. Stoll
*Assistant Examiner*—Joseph D. Anthony

[57] ABSTRACT

Oxazolidinone compounds useful as fungicides of Formula I

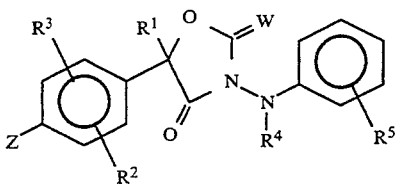

I wherein:
W is O or S;
Z is $-(CH_2)_nOR^6$ or $-OCH(R^{11})(CH_2)_mR^6$;
n is 0–4;
m is 0—3;
$R^6$ is phenyl substituted with $C_3$–$C_8$ trialkylsilyl; or quinolinyl, isoquinolinyl, quinolinyl, quinolinyl, quinoxalinyl, benzo[b]thienyl, benzo[b]furanyl, indoly, N-methylindolyl, isoindolyl, indolizinyl, indazolyl, benzimidazolyl, benzthiazolyl, benzoxazolyl, benzisothiazolyl, or benzisooxazolyl each optionally substituted; and
$R^1$, $R^2$, $R^3$, $R_4$, $R_5$, and $R^{11}$ are defined in the disclosure, are disclosed.

9 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FUNGICIDAL OXAZOLIDINONES

This invention relates to a particular oxazolidinone compounds useful as fungicides, agriculturally suitable compositions contianing such compounds, and methods of use of such compounds or compositions as fungicides in crop plants.

WO93/18016 is drawn to the use of fungicidal compounds of Formula i

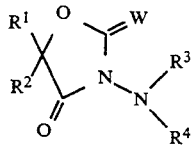

i wherein:

W is O or S; and $R^2$ is, in part, phenyl substituted with various heteroaryl groups.

The nature of the $R^2$ groups is different in the compounds of the present invention.

SUMMARY OF THE INVENTION

The present invention comprises compounds of Formula I including all geometric and stereoisomers, agricultural compositions containing them and use of the compounds and compositions as fungicides:

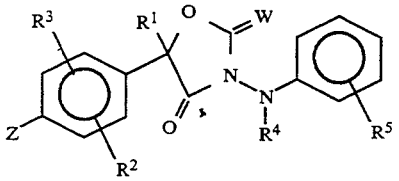

I wherein:

W is O or S;

$R^1$ is H; $C_1$–$C_4$alkyl; $C_1$–$C_4$ haloalkyl; $C_3$–$C_6$ cycloalkyl; $C_2$–$C_4$ alkenyl; or $C_2$–$C_4$ alkynyl;

$R^2$ is H; halogen; $C_1$–$C_4$alkoxy; trifluoromethyl; methylthio; or nitro;

$R^3$ is H or halogen;

$R^4$is H; methyl; or acetyl;

$R^5$ is H; trifluoromethyl; trifluoromethoxy; halogen; $C_1$–$C_4$ alkyl; $C_1$–$C_4$alkoxy; or cyano;

Z is $—(CH_2)_nOR^6$ or $—OCH(R^{11})(CH_2)_mR^6$;

n is 0–4;

m is 0–3;

$R^6$ is phenyl substituted with $C_3$–$C_8$ trialkylsilyl; or quinolinyl, isoquinolinyl, quinolinyl, quinazolinyl, quinoxalinyl, benzo[b]thienyl, benzo[b]furanyl, indolyl, N-methylindolyl, isoindolyl, indolizinyl, indazolyl, benzimidazolyl, benzthiazolyl, benzoxazolyl, benzisothiazolyl, or benzisooxazolyl each optionally substituted with one of $R^7$, $R^8$, or both $R^7$ and $R^8$;

$R^7$ and $R^8$ are each independently trifluoromethyl; trifluoromethoxy; nitro; $CO_2CH_3$; halogen; $C_1$–$C_4$ alkyl; $C_1$–$C_4$ alkoxy; or cyano; or phenoxy substituted with one of $R^9$, $R^{10}$, or both $R^9$ and $R^{10}$;

$R^9$ is halogen; $C_1$–$C_4$alkyl; $C_1$–$C_4$ alkoxy; trifluoromethyl; methylthio; or nitro;

$R^{10}$ is halogen; and $R^{11}$ is H; methyl; or ethyl;

and the agriculturally suitable salts thereof; provided that (i) when $R^2$ is other than H or F, the $R^2$ is substituted on the carbon atom of the phenyl ring adjacent to the carbon bearing the oxazolidinone ring; and (ii) when Z is $—CH_2OR^6$ or $—OCH(CH_3)R^6$, then $R^6$ is other than indolyl, N-methylindolyl, benzo[b]furanyl, benzo[b]thienyl, quinolinyl, or isoquinolinyl.

DETAILED DESCRIPTION OF THE INVENTION

In the above recitations, the term "alkyl", used either alone or in compound words such as "alkylthio" or "haloalkyl" denotes straight-chain or branched alkyl; e.g., methyl, ethyl, n-propyl, i-propyl, or the different butyl, pentyl or hexyl isomers. "Alkenyl" denotes straight-chain or branched alkenes; e.g., 1-propenyl, 2-propenyl, and the different butenyl, pentenyl and hexenyl isomers. "Alkenyl" also denotes polyenes such as 1,3-hexadiene and 2,4,6-heptatriene. "Alkynyl" denotes straight-chain or branched alkynes; e.g. ethynyl, 1-propynyl and the different butynyl, pentynyl and hexynyl isomers. "Alkynyl" can also denote moieties comprised of multiple triple bonds; e.g., 2,7-octadiyne and 2,5,8-decatriyne. "Alkoxy" denotes, for example, methoxy, ethoxy, n-propyloxy, isopropyloxy and the different butoxy, pentoxy and hexyloxy isomers. The term "halogen", either alone or in compound words such as "haloalkyl", denotes fluorine, chlorine, bromine or iodine. Further, when used in compound words such as "haloalkyl", said alkyl may partially or fully substituted with halogen atoms which may be the same or different. Examples of "haloalkyl" include $F_3C$, $ClCH_2$, $CF_3CH_2$and $CF_2CCl_2$. The total number of carbon atoms in a substituent group is indicated by the "$C_i$–$C_j$" prefix where i and j are numbers from 1 to 8.

In the above recitations, when a compound of Formula I is comprised of one or more sulfur-, or oxygen-containing rings (e.g, benzo[b]furanyl and benzo[b]thienyl, rings), all bonds to these heterocycles are made through the carbon atom(s) of the moieties. The same is the case for compounds bearing a nitrogen containing ring such as quinoline or quinazoline wherein a bond to the nitrogen atom would form an alkylamonium salt. However, compounds wherein $R^6$ is an optionally substituted indolyl, isoindolyl, benzimidazolyl, or indazolyl ring can have bonds through the nitrogen atom.

Examples of some of the heterocyclic $R^6$ substituents defined above are illustrated below. As indicated above, each of these substituents is optionally substituted with one of $R^7$, $R^8$, or both $R^7$ and $R^8$.

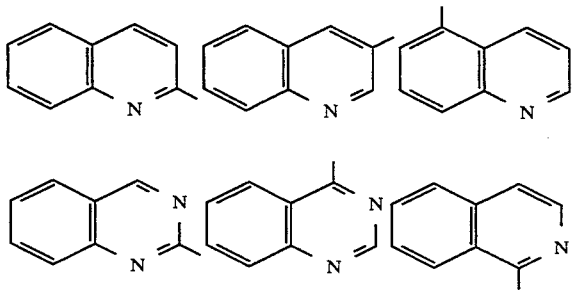

-continued

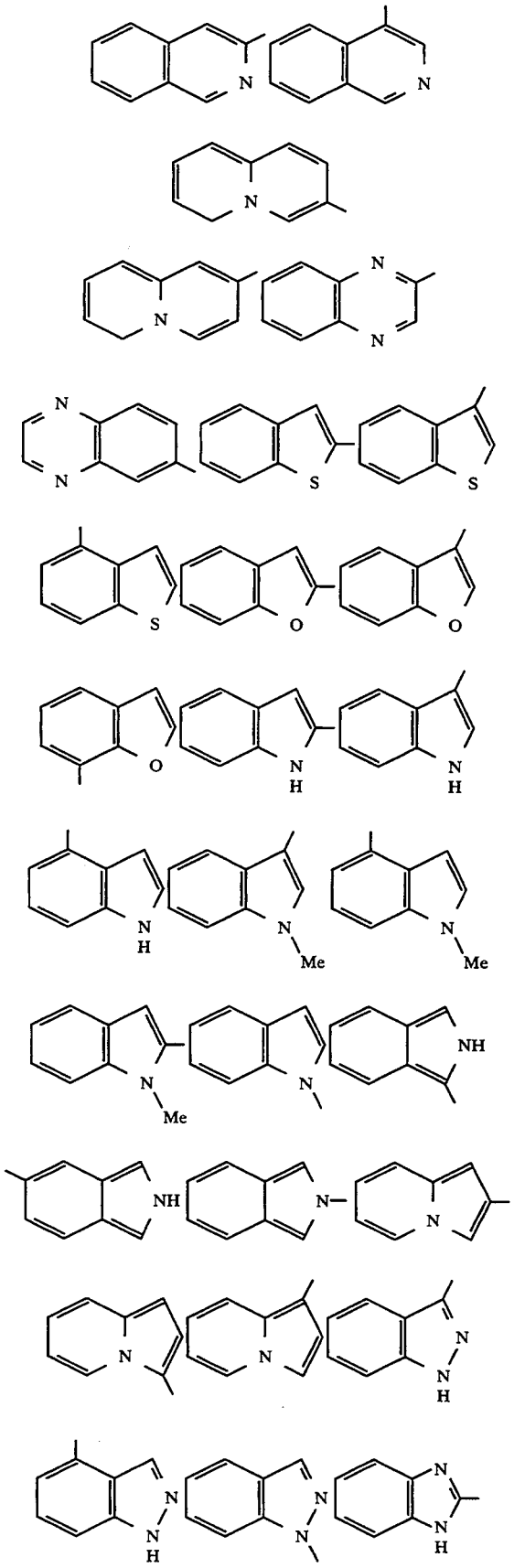

-continued

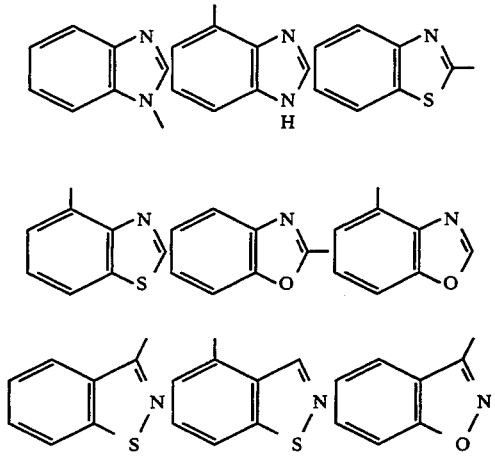

Preferred compounds, compositions containing them, and methods of their use for reasons of better activity and/or ease of synthesis are:

Preferred 1. Compounds of Formula I above wherein:

W is O;

$R^1$ is H; $C_1$–$C_4$alkyl; $C_1$–$C_4$haloalkyl; allyl; or propargyl;

$R^2$ is H; halogen; or $C_1$–$C_4$ alkyl;

$R^3$ is H or halogen;

$R^4$ is H or methyl;

$R^5$ is H; halogen; or $C_1$–$C_4$ alkyl;

Z is —$OCH(R^{11})(CH_2)_mR^6$; and $R^6$ is phenyl substituted with $C_3$–$C_8$ trialkylsilyl; or quinolinyl, isoquinolinyl, quinazolinyl, benzo[b]-thienyl, benzo[b]furanyl, indolyl, N-methylindolyl, indazolyl, benzimidazolyl, benzthiazolyl, or benzoxazolyl, each optionally substituted with one of $R^7$ or $R^8$ or both $R^7$ and $R^8$.

Preferred 2. Compounds of Formula I above wherein:

W is O;

$R^1$ is H; $C_1$–$C_4$ alkyl; $C_1$–$C_4$ haloalkyl; allyl; or propargyl;

$R^2$ is H; halogen; or $C_1$–$C_4$ alkyl;

$R^3$ is H or halogen;

$R^4$ is H or methyl;

$R^5$ is H; halogen; or $C_1$–$C_4$ alkyl;

Z is —$(CH_2)_nOR^6$; and $R^6$ is phenyl substituted with $C_3$–$C_8$ trialkylsilyl; or quinolinyl, isoquinolinyl, quinazolinyl, benzo[b]-thienyl, benzo[b]furanyl, indolyl, N-methylindolyl, indazolyl, benzimidazolyl, benzthiazolyl, or benzoxazolyl, each optionally substituted with one of $R^7$, $R^8$, or both $R^7$ and $R^8$.

Preferred 3. Compounds of Preferred 1 above wherein:

$R^1$ is methyl;

$R^2$, $R^3$, $R^4$, $R^5$ and $R^{11}$ are each independently H; and m is 0.

Preferred 4. Compounds of Preferred 2 wherein:

$R^1$ is methyl;

$R^2$, $R^3$, $R^4$, and $R^5$ are independently H; and n is 0.

Specifically preferred for greatest fungicidal activity and/or ease of synthesis are:

5-methyl-3-(phenylamino)-5-[4-[[2-(trimethylsilyl)-phenyl]methoxy]phenyl]-2,4-oxazolidinedione; and 5-[4-(2-benzoxazolyloxy)phenyl]-5-methyl-3-(phenylamino)-2,4-oxazolidinedione.

It is recognized that some reagents and reaction conditions described below for preparing compounds of Formula I may not be compatible with some functionalities claimed for $R^1$, $R^2$, $R^3$, $R^4$, $R^5$, W and Z. In these cases, the incorporation of protection/deprotection sequences in the synthesis may be necessary in order to obtain the desired products. The cases in which protecting groups are necessary, and which protecting group to use, will be apparent to one skilled in chemical synthesis.

In the following description of the preparation of compounds of Formula I, compounds denoted as Formula Ia and Ib are various subsets of the compounds of Formula I, and all substituents for Formula Ia and Ib are as defined above for Formula I. In addition of substituents for compounds of Formulae 1–12 are as defined above for Formula I or are defined in the text.

Compounds of this invention can exist as one or more stereoisomers. The various stereoisomers include enantiomers, diastereomers and geometric isomers. One skilled in the art will appreciate that one stereoisomer may be more active than the others and how to separate said stereoisomers. Accordingly, the present invention comprises mixtures, individual stereoisomers, and optically active mixtures of compounds of Formula I as well as agriculturally suitable salts thereof.

The compounds of Formula I can be prepared as described below in Schemes 1–5.

Several methods are taught in the literature for the preparation of oxazolidinones of Formula I (Schemes 1and 2). Geffken et al., U.S. Pat. No. 5,223,523 incorporated herein by reference, discloses the preparation of oxazolidinones by treating dioxazinediones of Formula 1 with a substituted hydrazine of Formula 2 as illustrated in Scheme 1. The preparation of the starting dioxazinediones of Formula 1 is also described therein. Substituted hydrazines of Formula 2 are either commercially available or can be prepared by literature methods (J. Timberlake; J. Stowell); *The Chemistry of the Hydrazo, Azo, and Azoxy Groups* (S. Patai, Ed.) John Wiley and Sons, Ltd., London (1975), p. 69; Demers, J. P.; Klaubert, D. J.; *Tetrahedron Lett.* (1987), 4933.

Scheme 1

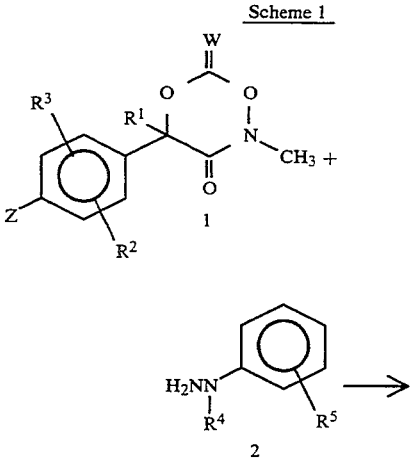

-continued

Scheme 1

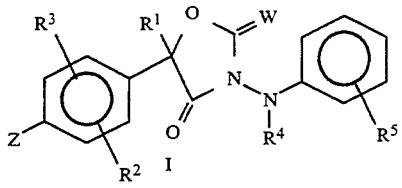

U.S. Pat. No. 5,223,523 also describes the desulfurization of 2-thioxo-4-oxazolidinones of Formula Ia to yield 2,4-oxazolidinediones of Formula Ib as shown in Scheme 2. Suitable desulfurizing agents include aqueous Oxone® ($KHSO_5$) and aqueous silver nitrate.

Scheme 2

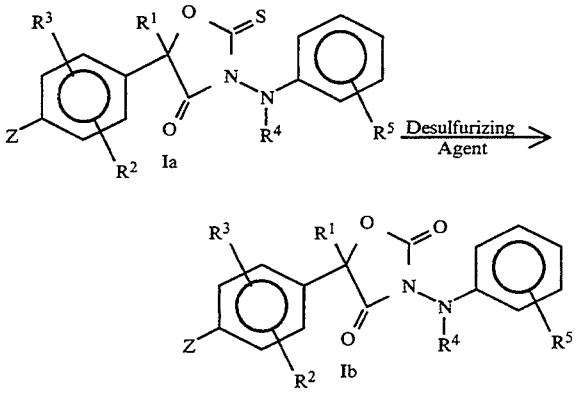

2-Thioxo-4-oxazolidinones of Formula Ia can be perpared by one or both of the methods described in detail in the literature and incorporated herein by reference (Geffken, D.; *Z. Naturforsch.* (1983), 38b, 1008; Geffken, D.; *Arch. Pharm.*, (1982) 315, 802; U.S. Pat. No. 5,223,523 and U.S. Pat. No. 4,957,933).

In addition, compounds of Formula I can be prepared by the methods outlined in Scheme 3. These procedures involve treatment of a 2-hydroxycarboxylic acid ester of Formula 4 with a carbonylating agent of Formula 6 to produce compounds of Formula 5, followed by conversion of 5 to the oxazolidinone of Formula I by treatment with a substituted hydrazine 2. In the carbonylating agent of Formula 6, U can be chlorine, 1-imidazolyl, 1,2,4-triazolyl or other suitable leaving group. The Y-group in esters of Formula 4 can be $C_1$–$C_4$ alkyl, $C_3$–$C_{12}$ cycloalkyl, $C_6$–$C_7$ cycloalkylalkyl, $C_2$–$C_4$ alkoxyalkyl, or phenylmethyl. Preferred for ease of synthesis and lower expense are esters in which Y is $C_1$–$C_4$ alkyl.

Scheme 3

Step 1

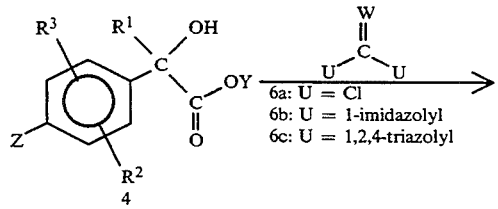

-continued

Scheme 3

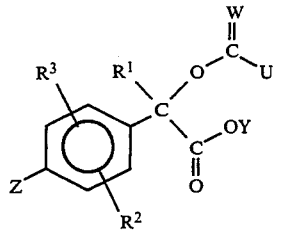

5a: U = Cl
5b: U = 1-imidazolyl
5c: U = 1,2,4-triazolyl

Step 2

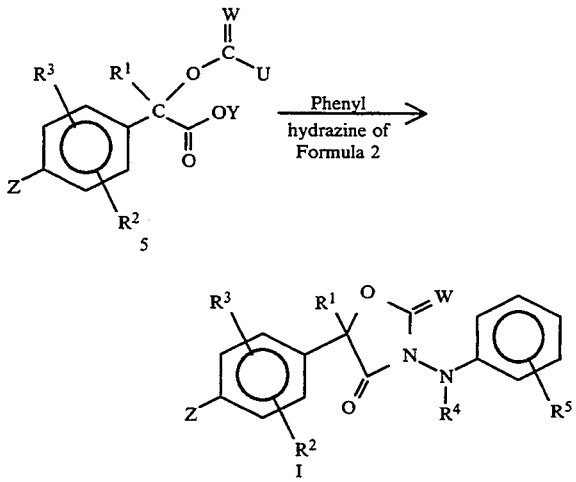

I

Y = $C_1$–$C_4$ alkyl, $C_3$–$C_4$ alkenyl, $C_3$–$C_{12}$ cycloalkyl, $C_6$–$C_7$ cycloalkylalkyl, $C_2$–$C_4$ alkoxyalkyl, $PhCH_2$ The preferred method using compounds of Formula 5a as the intermediate are those in which W is O. For the preparation of the compounds of Formula 5a (U=Cl), the alcohols of Formula 4 are dissolved in an inert solvent such as methylene chloride or 1-chlorobutane, and treated with a tertiary-amine base such as triethylamine, pyridine, and N,N-diisopropylethylamine, at a temperature from −60° to 30° C. To this mixture is added phosgene (6a, W=O) or thiophosgene (6a, W=S) to provide chloroformates of Formula 5a. Phosgene can be added as a gas or dissolved in an inert solvent such as toluene and added in solution. When the reaction of Step 1 is complete, the resulting mixture is poured into a water-immiscible solvent and washed with dilute aqueous mineral acid, water, and brine. The organic liquid phase is dried and evaporated to yield products of Formula 5a.

The compounds represented by Formula 5b (U=1-imidazolyl) can be prepared using 1,1'-carbonyldiimidazole (6b, W=O, CDI) or 1,1'-thiocarbonyldiimidazole (6b, W=S). The preparation using CDI is described below. The alcohols of Formula 4 are dissolved in an inert solvent in which the CDI has sufficient solubility at the reaction temperature. Methylene chloride, 1-chlorobutane and toluene are three of many suitable inert solvents. The CDI is added as a solid or as a solution in an inert solvent at temperatures from 0° to 100° C.

When the reaction is complete, the resulting mixture is poured into a water-immiscible solvent and washed successively with dilute mineral acid, water, and brine. The organic liquid phase is separated, dried, and evaporated to isolate the product.

Compounds of Formula 5c (U=1,2,4-triazolyl) are preared by treating esters of Formula 4 with 1,1'-carbonylditrizole (CDT) or 1,1'-thiocarbonylditrizole as described above for CDI. Additional base may be added to accelerate the reaction. Suitable bases include trialkylamine, imidazole, pyridine, picoline or other substituted pyridine, or mixtures thereof. For both CDI and CDT, the carbonylating agent of Formula 5 can be added as a pure compound, a solution of the pure compound in an inert solvent, or prepared in situ in the presence of the ester of Formula 4. For example, the CDI can be first prepared by treatment of a solution of imidazole in an inert solvent with phosgene as described by Staab and Wendel (*Org. Syntheses.* Coll. Vol. 5, 201, (1973)), and then treated in situ with the alcohol of Formula 4 to afford 5b.

In some cases, isolation of compounds of Formula 5 is not ncessary. For example, after the formation of the compound of Formula 5 is complete, the compounds can be treated in situ with a hydrazine of Formula 2 as described below for Step 2.

As illustrated in Step 2 of Scheme 3, compounds of Formula 5 are dissolved in an inert solvent such as methylene chloride, 1-chlorobutane, or THF and treated with a hydrazine of Formula 2 at a temperature from 0° to 80° C. When U is Cl as shown in Formula 5a, about one equivalent of a tertiary-amine base such as triethylamine, N,N-diethylaniline, N,N-diisopropylethylamine, or a second equivalent of the hydrazine can be added. When U=1-imidazolyl or 1,2,4-triazolyl as in Formulae 5b and 5c, about one equivalent of an acid can be added to accelerate the reaction. Suitable acids for catalyzing the reaction are selected from the group consisting of alkyl and aryl carboxylic acids, trialkylammonium halides and combinations thereof. The preferred acids are acetic acid and triethylammonium chloride. The most preferred acid is acetic acid.

Upon completion of the reaction of Step 2, the oxazolidinone of Formula I is isolated by evaporation of the aforementioned inert solvent, and purified by dissolving the residue in a water-immiscible solvent such as ether or methylene chloride, washing with mineral acid, aqueous base, and water, drying, and evaporating the extraction solvent. Crystallization or chromatography can be utilized for additional purification if desired.

For reasons of higher yields and lower expense, the methods of preparing compounds of Formula I from compounds of Formula 5b (U=1-imidazolyl) or 5c (U=1,2,4-triazolyl) are preferred to the methods of preparing I from 5a.

The 2-hydroxycarboxylic acid esters of Formula 4 can be prepared by a number of methods known in the literature.

(1) They can be formed from the corresponding 2-hydroxycarboxylic acids by esterification as is well known in the literature. The 2-hydroxycarboxlic acids can be prepared from ketones or aldehydes by formation of cyanohydrins, then hydrolysis, as is also known. For example, *Org. Syntheses,* Coll. Vol. 4, 58 (1968) teaches the preparation of atrolactic acid from acetophenone.

(2) The esters can also be synthesized from aldehyde and ketone cyanohydrins by treatment with alcohols in the presence of HCl to afford the iminoether hydrochlorides, followed by hydrolysis.

(3) A third method known for preparing 2-hydroxycarboxylic acids and esters involves treating 2-keto-acids or 2-keto-esters with nucleophilic-organometallic reagents such as Grignard reagents, and alkyl- and aryl-lithium reagents. For example, R. G. Salomon et al. teaches the preparation of some esters of Formula 4 by the addition of aryl-Grignard reagents to pyruvate esters (*J. Org. Chem.* (1982), 47, 4692). Similarly, some 2-hydroxycarboxylic acids may be prepared by the regioselective nucleophilic addition of an aryl organometallic reagent to the metal salt (e.g., sodium salt) of pyruvic acid.

(4) Another method described in the literature for preparing some 2-aryl-2-hydroxyesters and acids is by acylation of aromatic rings with activated carbonyl compounds in the presence of a protic or Lewis acid. Aromatic substrates capable of undergoing reactions of this type are benzene, diphenyl ether, furan and other aromatic compounds known to be of sufficient reactivity to undergo Friedel-Crafts-type reactions. In the case of mono-substited benzene derivatives, the acylation occurs preferentially, but not necessarily exclusively, para to the point of attachment of the substituent. For example, see *Org. Syntheses,* Coll. Vol. 3, 236, (1955), Salomon et al., *J. Org. Chem.,* (1982), 47, 4692, and U.S. Pat. No. 4,922,010.

Carbonyl compounds known to undergo this reaction include pyruvate esters and acids, glyoxylate esters and acids, and diesters of oxomalonates. The acids used in the acylation reaction can either be protic in nature, for example, a mixture of acetic and sulfuric acid, or a Lewis acid such as aluminum chloride, tin tetrachloride, titanium tetrachloride, or other Lewis acid known to effect Friedel-Crafts-type reactions. The acid can be used either catalytically or in excess. In some cases, the acid may react destructively with the carbonyl substrate and excess carbonyl compound must be used.

The acylation can be conducted neat or in a solvent known by one skilled in the art to be suitable for Friedel-Crafts reactions, for example, methylene chloride, carbon disulfide, and nitrobenzene. The reaction may be conducted from −50° to 100° C. The specific choice of acid, solvent, temperature, and reaction time will depend on the carbonyl and aromatic substrates to be reacted.

One skilled in the art will recognize that a substituent residing on the C-5 phenyl ring (i.e., $R^2$, $R^3$, and Z) may be incompatible with the conditions in the methods described above for the preparation of the 2-hydroxyester functionality. In some instances, it may be desirable to construct the phenyl unit after the introduction of the hydroxyester moiety. For example, the formation of the $Z=—OCH(R^{11})(CH_2)_mR^6$ functionality can be synthesized with the hydroxyester functionalities already in place as illustrated in Scheme 4.

Scheme 4

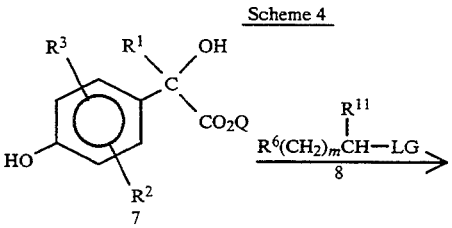

-continued

Scheme 4

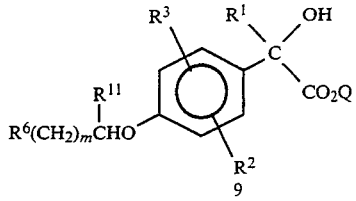

Q = $C_1$–$C_4$ alkyl, $C_1$–$C_4$ alkenyl, benzyl
LG = Cl, Br, I, $OS(O)_2CH_3$, $OS(O)_2$(4-Me—Ph)

For other hydroxyester starting materials, the formation of the $Z=—(CH_2)_nOR^6$ functionality (wherein n is other than 0 when $R^6$ is phenyl substituted with trialkylsilyl) can be prepared as illustrated in Scheme 5.

Scheme 5

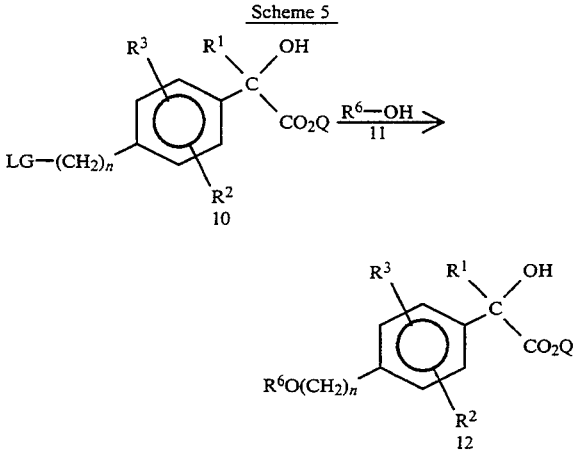

Q = $C_1$–$C_4$ alkyl, $C_1$–$C_4$ alkenyl, benzyl
LG = Cl, Br, I, $OS(O)_2CH_3$, $OS(O)_2$(4-Me—Ph)

The formation of ethers is well known in the chemical literature. The classical method for the preparation of ethers, the Williamson ether synthesis, involves reaction of an alkoxide, such as alkoxides derived from compounds of Formulae 7 and 11, with an electrophile, such as compounds of Formulae 8 and 10, in an inert solvent. A variety of electrophiles of Formulae 8 and 10 are commercially available or can be prepared by known methods (e.g., see Hudlicky, M.; Hudlicky, T. In *The Chemistry of Functional Groups,* Patai, S; Rappoport, Z., Eds.; Supplement D, Pt 2; pp. 1021–1172). For example, a chemoselective O-alkylation of a compound of Formula 7 in Scheme 4 is accomplished by heating a mixture of a compound of Formula 7 with an optionally substituted arylmethyl halide of Formula 8 (m=0; LG=Cl, Br, or I) of Formula 8 and a base (e.g., potassium carbonate) in an inert solvent.

One skilled in the art will recognize that the use of protecting groups may be necessary in order to prepare the hydroxyesters of Formulae 7 and 10. For example in the case of compounds of Formula 7, a protecting group may be necessary to mask the acidic proton on the phenyl hydroxy group during the introduction of the hydroxyester group. A trialkylsilyl protecting group is preferred in this regard (see *Synthesis,* (1982), 817 and *Tetrahedron Lett.* (1979), 3981).

EXAMPLE 1

Step A: Preparation of 2-(4-(6-chloro-2-benzothiazolyloxy)phenyl)lactate

A mixture of ethyl 2-(4-hydroxyphenyl)lactate (1.26 g, 6.0 mmol), powdered $K_2CO_3$ (4.14 g, 30 mmol) and 2,6-dichlorobenzothiazole (1.22 g, 6.0 mmol) in dry acetone was heated at a gentle reflux for 36 h at which time thin layer chromatography indicated that no starting material remained. Solvent was evaporated and the residue was suspended in diethyl ether (150 mL) and washed with $H_2O$ (two-times with 50 mL) and brine (two-times with 50mL). The aqueous washes were extracted with diethyl ether (50mL) and the ether phases were combined, dried ($MgSO_4$) and concentrated under vacuum to yield crude product, 2.19 g, which was subjected to purification by column chromatography (75 g $SiO_2$ eluting with 3:2:5 diethyl ether/$CH_2Cl_2$hexanes) thereby affording the product of Step A as a clear oil, 1.56 g; (69%); IR (neat): 3570, 3504, 1743, 1524, 1499 $cm^{-1}$; $^1H$ NMR ($CDCl_3$); δ7.75–7.65 (m,4H), 7.4 (d,3H), 4.4–4.2 (m,2H), 3.9 (s,1H), 1.8 (s,3H), 1.3 (t,3H).

Step B: Preparation of 5-(4-(6-Chloro-2-benzothiazolyloxy)phenyl)-5-methyl-3-(phenylamino)-2,4-oxazolidinedione To a solution of 2-(4-(6-chloro-2-benzothiazolyloxy)-phenyl)lactate (1.56 g, 4.1 mmol( in $CH_2Cl_2$ (20 mL) was added 1,1'-carbonyldiimidazole (0.86 g, 5.3 mmol) and the resulting mixture was heated at reflux overnight. The solution was diluted with $CH_2Cl_2$ (20 mL) and then washed with $H_2O$ (two-times with 20 mL) and brine (20 mL). The organic phase was dried ($MgSO_4$) and concentrated under vacuum. The residue was dissolved in $CH_2Cl_2$ (20 mL) and $PhNHNH_2$ (0.77 g, 7.8 mmol) and acetic acid (0.45 mL, 7.8 mmol) were added and the resulting mixture was stirred at room temperature until thin layer chromatography indicated no imidazolide remained, approximately 36 h. The mixture was diluted with $CH_2Cl_2$ (20 mL) and washed with 1N aqueous HCl (10 mL) and $H_2O$ (10 mL). The organic phase was dried ($MgSO_4$) and concentrated under vacuum to yield a red solid, 1.92 g, which was subjected to purification by column chromatography (140 g $SiO_2$ eluting with 3:2:5 diethyl ether/$CH_2Cl_2$/hexanes increasing to a ratio of 4:3:3 diethyl ether/$CH_2Cl_2$/hexanes thereby affording the product of Step B as a light yellow powder, 0.37 g; (19%); m.p. 207°–209° C.; IR (mineral oil): 1820, 1755, 1594, 1245 $cm^{-1}$; $^1H$ NMR ($CDCl_3$); δ7.7 (m,3H), 7.65 (d,1H), 7.5 (d,2H), 7.4 (d,1H), 7.3 (m,2H), 7.0 (t,1H), 6.8 (d,2H), 6.1 (s,1H), 2.0 (s,3H).

EXAMPLE 2

Step A: Preparation of 2-Bromo-(Trimethylsilyloxymethyl)benzene

To a solution of 2-bromobenzyl alcohol (4.86 g, 26 mmol) in $CH_2Cl_2$ (80 mL) cooled to 0° C. was added $Me_3SiCl$ (3.12 g, 28.6 mmol), triethylamine (4.34 g, 31.2 mmol) and 4-N,N-dimethylaminopyridine (0.32 g, 2.6 mmol). The cooling bath was removed and the mixture was allowed to warm to room temperature and stirred whereupon reaction was determined by thin layer chromatography to be completed after 2 h. The solution was washed with 1N aqueous HCl (30 mL) $H_2O$ (30 mL) and saturated aqueous $NaHCO_3$ (30 mL). The organic phase was dried ($MgSO_4$) and concentrated under vacuum to provide a brown oil, 6.67 g. Purification by column chromatography (80 g $SiO_2$ eluted with 10% diethyl ether/hexane) afforded the product of Step A as a clear, yellow oil, 5.94 g, (88%); IR (neat): 2956, 2897, 1441, 1251 $cm^{-1}$; $^1H$ NMR ($CDCl_3$); δ7.5 (dd, 2h), 7.3 (t,1H), 7.1 (t,1H), 4.7 (s,2H), 0.2 (s,9H).

Step B: Preparation of 2-(Trimethylsilyl)benzyl alcohol

A stirred solution of 2-bromo-(trimethylsilyloxymethyl)benzene (2.85 g, 11 mmol) in dry tetrahydrofuran (50 mL) was cooled to −70° C. and sec-butyllithium (12.1 mmol) was slowly added via syringe. The resulting mixture was stirred at −70° C. for 1 h, then allowed to warm to 0° C. Saturated aqueous $NH_4Cl$ (10 mL) was added and the resulting mixture was diulted with diethyl ether (50 mL). Water was added to dissolve precipitated solids and the aqueous phase was removed. The organic phase was washed with brine (50 mL), dried ($MgSO_4$) and concentrated under vacuum to yield a clear oil, 2.16 g. Column chromatography (80 g $SiO_2$ eluting with 20% ethyl acetate/hexanes) afforded the product of Step B as a clear, light yellow oil, 1.21 g; (61%); IR (neat): 3324, 2953, 2896, 1249 $cm^{-1}$; $^1H$ NMR ($CDCl_3$): δ7.55 (d,1H), 7.5 (d,1H), 7.4 (t,1H), 7.3 (t,1H), 4.7 (d,2H), 1.6 (t,1H), 0.35 (s,9H).

Step C: Preparation of 2-(Trimethylsilyl)benzyl bromide

Bromine (1.07 g, 6.7 mmol) was slowly added to a cooled solution of triphenylphosphine (1.83 g, 7.0 mmol) in acetonitrile to maintain a temperature less than or equal to 5° C. A solution of 2-(trimethylsilyl)-benzyl alcohol in acetonitrile (10 mL) was slowly introduced and the resulting mixture was allowed to warm to room temperature and stir. Thin layer chromatography after 20 min indicated no starting material remained. The mixture was diluted with diethyl ether (50 mL) and washed with $H_2O$ (two-times with 20 mL), dried ($MgSO_4$) and concentrated under vacuum to yield an opaque oil, 2.5 g. Purification by column chromatography (100 g $SiO_2$ eluting with hexanes) provided the product of Step C as a clear, colorless oil, 1.12 g; (69%); IR (neat): 2954, 1250, 1216, 1110 $cm^{-1}$; $^1H$ NMR ($CDCl_3$); δ7.5–7.3 (m,4H), 4.6 (s,2H), 0.4 (s,9H).

Step D: Preparation of Ethyl 2-(4-(2-trimethylsilylbenzyloxy)phenyl)lactate

A mixture of ethyl 2-(4-hydroxyphyenyl)lactate (0.97 g, 4.6 mmol), powdered $K_2CO_3$ (0.95 g, 6.9 mmol) and 2-(trimethylsilyl)benzyl bromide (1.12, 4.6 mmol) in dry dimethylformamide (5 mL) was stirred at room temperature for 16 h at which time thin layer chromatography indicated that no starting material remained. The reaction mixture was diluted with diethyl ether (40 mL) and washed with $H_2O$ (two-times with 20 mL) and brine (two-times with 20mL). The aqueous washes were extracted with diethyl ether (30 mL) and the ether phases were combined, dried ($MgSO_4$) and concentrated under vacuum to yield the product of Step D as a yellow oil, 0.93 g, (55%); IR (neat): 3512, 2955, 1726, 1509 $cm^{-1}$; $^1H$ NMR ($CDCl_3$); δ7.6 (d, 1H), 7.5 (d, 3H), 7.4 (t,1H), 7.35 (m,1H), 6.95 (d,2H), 5.1 ) (s,2H), 4.2 (m,2H), 3.75 (s,1H), 1.75 (s,3H), 1.23 (t,3H), 0.35 (s,9H).

Step E: Preparation of 5-methyl-3(phenylamino)-5[4-[[2-(trimethylsilyl)-phenyl]-methoxy]phenyl]-2,4-oxazolidinedione A solution of ethyl 2-(4-(2-trimethylsilylbenzyloxy)-phenyl)lactate (0.93 g, 2.5 mmol) in $CH_2Cl_2$ (15 mL) was treated with 1,1'-carbonyldiimidazole (0.53 g, 3.3 mmol) and the resulting mixture was heated overnight. The resulting solution was diluted with diethyl ether (45 mL) and washed with $H_2O$ (two-times with 15 mL), brine (15 mL), dried ($MgSO_4$) and concentrated under vacuum. The residue was dissolved in $CH_2Cl_2$ and to the solution was added $PhNHNH_2$ (0.46 g, 4.3 mmol) and acetic acid (0.24 mL, 4.3 mmol). The resulting mixture was stirred at room temperature for 60 h after-which time the mixture was diluted with $CH_2Cl_2$ (20 ml) and washed with 1N aqueous HCl (10 mL) and $H_2O$ (10 mL). The organic phases were dried ($MgSO_4$) and concentrated under vacuum to yield a residue which was subjected to column chromatography (75 g $SiO_2$ eluted with 2:2:6 diethyl ether/$CH_2Cl_2$/hexanes) thereby affording the product of Step E as a yellow powder, 0.62 g; (54%); m.p. 112°-114° C.; IR (mineral oil): 3308, 1738, 1245 $cm^{-1}$; $^1H$ NMR ($CDCl_3$): δ7.6 (d,1H), 7.55 (d,2H), 7.5 (d,1H), 7.45 (t,1H), 7.35 (t,1H), 7.25 (m,2h), 7.0 (d,3H), 6.75 (d,2H), 6.05 (s,1H), 5.1 (s,2h), 2.0 (s,3H), 1.23 (t,3H), 0.3 (s,9H).

Formulation/Utility

Compounds of this invention will generally be used in formulation with an agriculturally suitable composition. The fungicidal compositions of the present invention comprise an effective amount of at least one compound of Formula I as defined above and at least one of (a) a surfactant, (b) an organic solvent, and (c) at least one solid or liquid diluent. Useful formulations can be prepared in conventional ways. They include dusts, granules, pellets, solutions, suspensions, emulsions, wettable powders, emulsifiable concentrates, dry flowables and the like. Sprayable formulations can be extended in suitable media and used at spray volumes from about one to several hundred liters per hectare. High strength compositions are primarily used as intermediats for further formulation. The formulations will typically contain effective amounts of active ingredient, diluent and surfactant within the following approximate ranges which add up 100 weight percent.

| | Weight Percent | | |
|---|---|---|---|
| | Active Ingredient | Diluent | Surfactant |
| Wettable Powders | 5–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, N.J. Typical liquid diluents and solvents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, (1964), list surfactants and recommended uses. All formulations can contain minor amounts of additives to reduce foam, caking, corrosion, microbiological growth, and the like.

Methods for formulating such compositions are well known. Solutions are prepared by simply mixing the ingredients. Fine solid compositions are made by blending and, usually, grinding as in a hammer mill or fluid energy mill. Water-dispersible granules can be produced by agglomerating a fine powder composition; see for example, Cross et al., *Pesticide Formulations,* Washington, D.C., 1988, pp. 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", *Chemical Engineering,* Dec. 4, 1967, pp. 147–148, *Perry's Chemical Engineer's Handbook,* 4th Ed., McGraw-Hill, New York, (1963), pp. 8–57 and following, and WO91/13546. Pellets can be prepared as described in U.S. Pat. No. 4,172,714. Water-dispersible and water-soluble granules can be prepared as taught in DE 3,246,493.

For further information regarding the art of formulation, see U.S. Pat. No. 3,235,361, Col. 6, line 16 through Col. 7, line 19 and Examples 10 through 41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc.,New York, (1961), pp. 81–96; and Hance et al., *Weed Control Handbook,* 8th Ed., Blackwell Scientific Publications, Oxford, (1989).

In the following Examples, all percentages are by weight and all formulations are prepared in conventional ways. Compound 1 is described in Index Table A hereinafter.

EXAMPLE A

| Wettable Powder | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

| Granule | |
|---|---|
| Compound 1 | 10.0% |
| attapulgite granules (low volative matter, 0.71/0.30 mm; U.S.S. No. 25–50 sieves) | 90.0%. |

EXAMPLE C

| Extruded Pellet | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

| Emulsifiable Concentrate | |
|---|---|
| Compound 1 | 20.0% |
| blend of oil soluble sulfonates and polyoxyethylene ethers | 10.0% |
| isophorone | 70.0%. |

The compounds of this invention are useful as plant disease control agents. The present invention therfore further comprises a method for controlling plant diseases caused by fungal plant pathogens comprising applying to the plant or portion thereof to be protected, or to the plant seed or seedling to be protected, an effective amount of a compound of Formula I or a fungicidal composition containing said compound. The compounds and compositions of this invention provide control of diseases caused by a broad spectrum of fungal plant pathogens in the Basidiomycte, Ascomycete, Oomycete and Deuteromycete classes. They are effective in controlling a broad spectrum of plant diseases, particularly foliar pathogens of ornamental, vegetable, field, cereal, and fruit crops. These pathogens include *Plasmopara viticola, Phytophthora infestans, Peronospora tabacina, Pseudoperonospora cubenis, Pythium aphanidermatum, Alternaria brassicae, Septoria nodorum, Septoria tritici, Cercosporidium personatum, Cercospora arachidicola, Pseudocercosporella herpotrichoides, Cercospora beticola, Botrytis cinerea, Monilinia fructicola, Pyricularia oryzae, Podosphaera leucotricha, Ventura inaequalis, Erysiphe graminis, Uncinula necatur, Puccinia recondita, Puccinia graminis, Hemeleia vastatrix, Puccinia striiformis, Puccinia arachidis, Rhizoctonia solani, Sphaerotheca fuliginea, Fusarium oxysporum, Verticillium dahliae, Pythium aphanidermatum, Phytophthora megasperma* and other generea and species closely related to these pathogens.

Preferred is a method of controlling *Plasmopara viticola* on grapes, *Phytophthora infestans* on potatoes and tomatoes and Septoria spp. on cereals.

Compounds of this invention can also be mixed with one or more other insecticides, fungicides, nematocides, bactericides, acaricides, semiochemicals, repellants, attractants, pheromones, feeding stimulants or other biologically active compounds to form a multi-component pesticide giving an even broader spectrum of agricultural protection. Examples of other agricultural protectants with which compounds of this invention can be formulated are: insectides such as acephate, avermectin B, azinphosmethyl, bifenthrin, biphenate, buprofezin, carbofuran, chlordimeform, chloropyrifos, cyfluthrin, deltamethrin, diazinon, diflubenzuron, dimethoate, esfenvalerate, fenpropathrin, fenvalerate, fipronil, flucythrinate, flufenprox, fluvalinate, fonophos, isofenphos, malathion, metaldehyde, metha-midophos, methidathion, methomyl, methoprene, methoxychlor, monocrotophos, oxamyl, parathion-methyl, permethrin, phorate, phosalone, phosmet, phosphamidon, pirimicarb, profenfos, rotenone, sulprofos, terbufos, tetrachlorvinphos, thiodicarb, tralomethrin, trichlorfon and triflumuron; fungicides such as benomyl, blasticidin S, bromuconazole, captafol, captan, carbendazim, chloroneb, chlorothalonil, copper oxychloride, copper salts, cymoxanil, cyproconazole, dichloran, diclobutrazol, diclomezine, difenoconazole, diniconazole, dodine, edifenphos, epxoyconazole fenarimol, fenbuconazole, fenpropidine, fenpropimorph, fluquinconazole, flusilazol, flutolanil, flutriafol, folpet, furalaxyl, hexaconazole, ipconazole, iprobenfos, iprodione, isoprothiolane, kasugamycin, mancozeb, maneb, mepronil, metalaxyl, metconazole, myclobutanil, neoasozin, oxadixyl, penconazole, pencycuron, phosethyl-Al, probenazole, prochloraz, propiconazole, pyrifenox, pyroquilon, sulfur, tebuconazole, tetraconazole, thiabendazole, thiophanate-methyl, thiuram, triadimefon, triadimenol, tricyclazole, uniconzole, validamycin and vinclozolin; nematocides such as aldoxycarb, fenamophos and fosthietan; bactericides such as oxytetracyline, streptomycin and tribasic copper sulfate; acaricides such as amitraz, binapacryl, chlorobenzilate, cyhexatin, dicofol, dienochlor, fenbutatin oxide, hexythiazox, oxythioquinox, propargite and tebufenpyrad; and biological agents such as *Bacillus thuringiensis* and baculovirus.

In certain instances, combinations with other fungicides having a similar spectrum of control but a different mode of action will be particularly advantageous for resistance management.

A preferred mixture comprises a compound of this invention mixed with cymoxanil to form a multi-component pesticide.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling.

Rates of application for these compounds can be influenced by many factors of the environment and should be determined under use conditions. Foliage can normally be protected when treated at a rate of less than 1 g/ha to 5,000 g/ha of active ingredient. Seed and seedlings can normally be protected when seed is treated at a rate of from 0.1 to 10 g per kilogram of seed.

The following TESTS demonstrate the control efficacy of compounds of this invention on specific pathogens. The pathogen control protection afforded by the compounds is not limited, however, to these species. See Index Table A for compound descriptions.

Test compounds were first dissolved in acetone in an amount equal to 3% of the final volume and then suspended at a concentration of 200 ppm in purified water containing 250 ppm of the surfactant Trem® 014 (polyhydric alcohol esters). The resulting test suspensions were then used in the following tests.

TEST A

The test suspension was sprayed to the point of runoff on wheat seedlings. The following day the seedlings were inoculated with a spore dust of *Erysiphe graminis f. sp. tritici,* (the causal agent of wheat powdery mildew) and incubated in a growth chamber at 20° C. for 7 days, after which disease ratings were made.

TEST B

The test suspension was sprayed to the point of runoff on wheat seedlings. The following day the seedlings were inoculated with a spore suspension *Puccinia recondita* (the causal agent of wheat leaf rust) and incubated in a saturated atmosphere at 20° C. for 24 h, and then moved to a growth chamber at 20° C. for 6 days, after which disease ratings were made.

TEST C

The test suspension was sprayed to the point of run-off on rice seedlings. The following day the seedlings were inoculated with a spore suspension of *Pyricularia oryzae* (the causal agent of rice blast) and incubated in a saturated atmosphere at 27° C. for 24 h, and then moved to a growth chamber at 30° C. for 5 days, after which disease ratings were made.

TEST D

The test suspension was sprayed to the point of run-off on tomato seedlings. The following day the seedlings were inoculated with a spore suspension of *Phytophthora infestans* (the causal agent of potato and tomato late blight) and incubated in a saturated atmosphere at 20° C. for 24 h, and then moved to a growth chamber at 20° C. for 5 days, after which disease ratings were made.

TEST E

The test suspension was sprayed to the point of run-off on grape seedlings. The following day the seedlings were inoculated with a sport suspension of *Plasmopara viticola* (the causal agent of grape downy mildew) and incubated in a saturated atmosphere at 20° C. for 24 h, moved to a growth chamber at 20° C. for 6 days, and then incubated in saturated atmosphere at 20° C. for 24 h, after which disease ratings were made.

TEST F

The test suspension was sprayed to the point of run-off on cucumber seedlings. The following day the seedlings were inoculated with a spore suspension of *Botrytis cinerea* (the causal agent of gray mold on many crops) and incubated in a saturated atmosphere at 20° C. for 48 h, and moved to a growth chamber at 20° C. for 5 days, after which disease ratings were made.

INDEX TABLE A

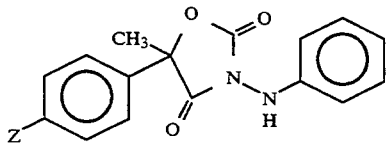

Ic

Compounds of Formula Ic wherein:

| Cmpd No. | Z | mp (°C.) |
|---|---|---|
| 1 | 2-[$(CH_3)_3Si$)Ph]$CH_2O$ | 112–114 |
| 2 | 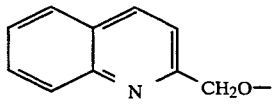 | 135–138 |
| 3 | 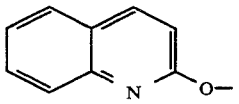 | 153–155 |
| 4 | 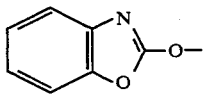 | 153–156 |

INDEX TABLE A-continued

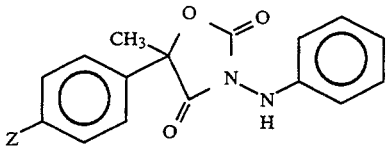

Ic

Compounds of Formula Ic wherein:

| Cmpd No. | Z | mp (°C.) |
|---|---|---|
| 5 | 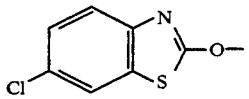 | 207–209 |

Results for Tests A–F are given in Table 1. In the table, a rating of 100 indicates 100% disease control and a rating of 0 indicates no disease control (relative to the controls). "—"=not tested.

TABLE 1

| Cmpd No. | Test A | Test B | Test C | Test D | Test E | Test F |
|---|---|---|---|---|---|---|
| 1 | 0 | 100 | 74 | 62 | 100 | 0 |
| 2 | 40 | 92 | 0 | — | 67* | 24 |
| 3 | 50 | 79 | 0 | — | 90* | 1 |
| 4 | 0 | 79 | 0 | 0 | 100 | 0 |
| 5 | 29 | 0 | 0 | — | 82* | 1 |

*Test was run at 40 ppm.

What is claimed is:

1. A compound of Formula I

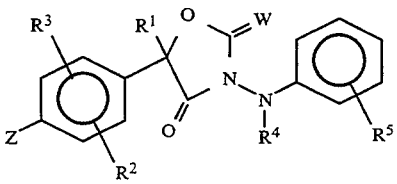

I wherein:

W is O or S;

$R^1$ is H; $C_1$–$C_4$ alkyl; $C_1$–$C_4$ haloalkyl; $C_3$–$C_6$ cycloalkyl; $C_2$–$C_4$ alkenyl; or $C_2$–$C_4$ alkynyl;

$R^2$ is H; halogen; $C_1$–$C_4$ alkyl; $C_1$–$C_4$ alkoxy; trifluoromethyl; methylthio; or nitro;

$R^3$ is H or halogen;

$R^4$ is H; methyl; or acetyl;

$R^5$ is H; trifluoromethyl; trifluoromethoxy; halogen; $C_1$–$C_4$ alkyl; $C_1$–$C_4$ alkoxy; or cyano;

Z is $—(CH_2)_nOR^6$ or $—OCH(R^{11})(CH_2)_mR^6$;

n is 0–4;

m is 0–3;

$R^6$ is phenyl substituted with $C_3$–$C_8$ trialkylsilyl; or quinolinyl, isoquinolinyl, quinolinyl, quinazolinyl, quinoxalinyl, benzo[b]thienyl, benzy[b]furanyl, indolyl, N-methylindolyl, isoindolyl, indolizinyl, indazolyl, benzimidazolyl, benathiazolyl, benzoxazolyl, benzisothiazolyl, or benzisooxazolyl each optionally substituted with one of $R^7$, $R^8$, or both $R^7$ and $R^8$;

$R^7$ and $R^8$ are each independently trifluoromethyl; trifluoromethoxy; nitro; $CO_2CH_3$; halogen; $C_1$–$C_4$ alkyl; $C_1$–$C_4$alkoxy; or cyano; or phenoxy substituted with one of $R^9$, $R^{10}$, or both $R^9$ and $R^{10}$;

$R^9$ is halogen; $C_1$–$C_4$ alkyl; $C_1$–$C_4$ alkoxy; trifuoromethyl; methylthio; or nitro;

$R^{10}$ is halogen; and $R^{11}$ is H; methyl; or ethyl;

and the agriculturally suitable salts thereof; provided that (i) when $R^2$ is other than H or F, the $R^2$ is substituted on the carbon atom of the phenyl ring adjacent to the carbon bearing the oxazolidinone ring; and (ii) when Z is $—CH_2OR^6$ or $—OCH(CH_3)R^6$, is other than indolyl, N-methylindolyl, benzo[b]furanyl, benzo[b]thienyl, quinolinyl, or isoquinolinyl.

2. A compound of claim 1, wherein

W is O;

$R^1$ is H; $C_1$–$C_4$alkyl; $C_1$–$C_4$ haloalkyl; allyl; or propargyl;

$R^2$ is H; halogen; or $C_1$–$C_4$ alkyl;

$R^3$ is H or halogen;

$R^4$ is H or methyl;

$R^5$ is H; halogen; or $C_1$–$C_4$ alkyl;

Z is $—OCH(R^{11})(CH_2)_mR^6$; and $R^6$ is phenyl substituted with $C_3$–$C_8$ trialkylsilyl; or quinolinyl, isoquinolinyl, quinazolinyl, benzo[b]thienyl, benzo[b]furanyl, indolyl, N-methylindolyl, indazolyl, benzimidazolyl, benzthiazolyl, or benzoxazolyl, each optionally substituted with one of $R^7$, $R^8$, or both $R^7$ and $R^8$.

3. A compound of claim 1, wherein

W is O;

$R^1$ is H; $C_1$–$C_4$ alkyl; $C_1$–$C_4$ haloalkyl; allyl; or propargyl;

$R^2$ is H; halogen; or $C_1$–$C_4$ alkyl;

$R^3$ is H or halogen;

$R^4$ is H or methyl;

$R^5$ is H; halogen; or $C_1$–$C_4$ alkyl;

Z is $—(CH_2)_nOR^6$; and $R^6$ is phenyl substituted with $C_3$–$C_8$ trialkylsilyl; or quinolinyl, isoquinolinyl, quinazolinyl, benzo[b]thienyl, benzo[b]furanyl, indolyl, N-methylindolyl, indazolyl, benzimidazolyl, benzthiazolyl, or benzoxazolyl, each optionally substituted with one of $R^7$, $R^8$, or both $R^7$ and $R^8$.

4. A compound of claim 2, wherein $R^1$ is methyl;

$R^2$, $R^3$, $R^4$, $R^5$ and $R^{11}$ are each independently H; and m is 0.

5. A compound of claim 3, wherein $R^1$ is methyl;

$R^2$, $R^3$, $R^4$and $R^5$ are each independently H; and n is 0.

6. A fungicidal composition comprising an effective amount of a compound of Formula I

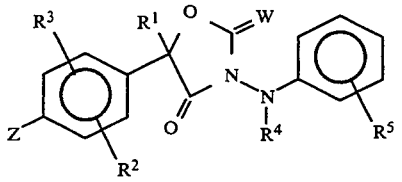

I wherein:

W is O or S;

$R^1$ is H; $C_1$–$C_4$ alkyl; $C_1$–$C_4$ haloalkyl; $C_3$–$C_6$ cycloalkyl; $C_2$–$C_4$ alkenyl; or $C_2$–$C_4$ alkynyl;

$R^2$ is H; halogen; $C_1$–$C_4$ alkyl; $C_1$–$C_4$ alkoxy; trifuloromethyl; methylthio; or nitro;

$R^3$ is H or halogen;

$R^4$ is H; methyl; or acetyl;

$R^5$ is H; trifuoromethyl; trifluoromethoxy; halogen; $C_1$–$C_4$ alkyl; $C_1$–$C_4$ alkoxy; or cyano;

Z is $—(CH_2)_nOR^6$ or $—OCH(R^{11})(CH_2)_mR^6$;

n is 0–4;

m is 0–3;

$R^6$ is phenyl substituted with $C_3$–$C_8$ trialkylsilyl; or quinolinyl, isoquinolinyl, quinolinyl, quinazolinyl, quinoxalinyl, benzo[b]thienyl, benzo[b]furanyl, indolyl, N-methylindolyl, isoindolyl, indolizinyl, indazolyl, benzimidazolyl, benzthiazolyl, benzoxazolyl, benzisothiazolyl, or benzisooxazolyl each optionally substituted with one of $R^7$, $R^8$, or both $R^7$ and $R^8$;

$R^7$ and $R^8$ are each independently trifluoromethyl; trifluoromethoxy; nitro; $CO_2CH_3$; halogen; $C_1$–$C_4$ alkyl; $C_1$–$C_4$ alkoxy; or cyano; or phenoxy substituted with one of $R^9$, $R^{10}$;

$R^9$ is halogen; $C_1$–$C_4$ alkoxy; trifluoromethyl; methylthio; or nitro;

$R^{10}$ is halogen; and $R^{11}$ is H; methyl; or ethyl;

and the agriculturally suitable salts thereof; provided that (i) when $R^2$ is other than H or F, the $R^2$ is substituted on the carbon atom of the phenyl ring adjacent to the carbon bearing the oxazolidinone ring; and (ii) when Z is $—CH_2OR^6$ or $—OCH(CH_3)R^6$, is other than indolyl, N-methylindolyl, benzo[b]furanyl, benzo[b]thienyl, quinolinyl, or isoquinolinyl;

and at least one of (a) surfactant, (b) an organic solvent, and (c) at least one solid or liquid diluent.

7. A method for controlling plant diseases caused by fungal plant pathogens comprising applying to the plant or portion thereof to be protected, or to the plant seed or seedlimg to be protected, an effective amount of a compound of Formula I

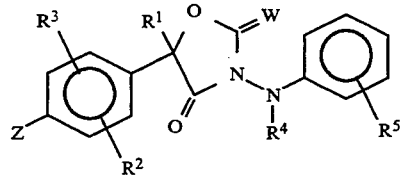

I wherein:

W is O or S;

$R^1$ is H; $C_1$–$C_4$ alkyl; $C_1$–$C_4$ haloalkyl; $C_3$–$C_6$ cycloalkyl; $C_2$–$C_4$ alkenyl; or $C_2$–$C_4$ alkynyl;

$R^2$ is H; halogen; $C_1$–$C_4$ alkyl; $C_1$–$C_4$ alkoxy; trifluoromethyl; methylthio; or nitro;

$R^3$ is H or halogen;

$R^4$ is H; methyl; or acetyl;

$R^5$ is H; trifluoromethyl; trifluoromethoxy; halogen; $C_1$–$C_4$ alkyl; $C_1$–$C_4$ alkoxy; or cyano;

Z is $—(CH_2)_nOR^6$ or $—OCH(R^{11})(CH_2)_mR^6$;

n is 0–4;

m is 0–3;

$R^6$ is phenyl substituted with $C_3$–$C_8$ trialkylsilyl; or quinolinyl, isoquinolinyl, quinolizinyl, quinazolinyl, quinoxalinyl, benzo[b]thienyl, benzo[b]furanyl, indolyl, N-methylindolyl, isoindolyl, indolizinyl, indazolyl, benzimidazolyl, benzthiazolyl, benzoxazolyl, benzisothiazolyl, or benzisooxazolyl each optionally substituted with one of $R^7$, $R^8$, or both $R^7$ and $R^8$;

$R^7$ and $R^8$ are each independently trifluoromethyl; trifluoromethoxy; nitro; $CO_2CH_3$; halogen; $C_1$–$C_4$ alkyl; $C_1$–$C_4$alkoxy; or cyano; or phenoxy substituted with one of $R^9$, $R^{10}$, or both $R^9$ and $R^{10}$;

$R^9$ is halogen; $C_1$–$C_4$ alkyl; $C_1$–$C_4$ alkoxy; trifluoromethyl; methylthio; or nitro;

$R^{10}$ is halogen; and $R^{11}$ is H; methyl; or ethyl;

and the agriculturally suitable salts thereof; provided that (i) when $R^2$ is other than H or F, the $R^2$ is substituted on the carbon atom of the phenyl ring adjacent to the carbon bearing the oxazolidinone ring; and (ii) when Z is $—CH_2OR_6$ or $—OCH(CH_3)R^6$, then $R^6$ is other than indolyl, N-methylindolyl, benzo[b]furanyl, benzo[b]thienyl, quinolinyl, or isoquinolinyl.

8. A method for controlling plant diseases caused by fungal plant pathogens comprising applying to the plant or portion thereof to be protected, or to the plant seed or seedling to be protected, an effective amount of a composition of claim 6.

9. The method of claim 7, wherein the fungal plant pathogens are caused by the plant pathogens *Phytophthora infestans* and *Plasmopara viticola*.

* * * * *